US009540310B2

(12) United States Patent
Lindekens et al.

(10) Patent No.: US 9,540,310 B2
(45) Date of Patent: Jan. 10, 2017

(54) RADIATION CURABLE (METH)ACRYLATED COMPOUNDS

(71) Applicant: Allnex Belgium S.A., Brussels (BE)

(72) Inventors: Luc Lindekens, Merchtem (BE); Thierry Randoux, Braine l'Alleud (BE); Ruben Cleymans, Halle (BE); Paul Gevaert, Geraardsbergen (BE)

(73) Assignee: ALLNEX BELGIUM S.A., Brussels (BE)

(*) Notice: Subject to any disclaimer, the term of this patent is extended or adjusted under 35 U.S.C. 154(b) by 196 days.

(21) Appl. No.: 14/372,387

(22) PCT Filed: Mar. 22, 2013

(86) PCT No.: PCT/EP2013/056125
§ 371 (c)(1),
(2) Date: Jul. 15, 2014

(87) PCT Pub. No.: WO2013/144028
PCT Pub. Date: Oct. 3, 2013

(65) Prior Publication Data
US 2014/0364530 A1    Dec. 11, 2014

(30) Foreign Application Priority Data
Mar. 30, 2012    (EP) ..................... 12162543

(51) Int. Cl.
C07C 69/60      (2006.01)
C08G 63/47      (2006.01)
C09D 167/07     (2006.01)
C07C 69/604     (2006.01)
C08G 18/81      (2006.01)
C09D 175/16     (2006.01)
C08G 18/42      (2006.01)
C07C 271/24     (2006.01)
C07D 493/04     (2006.01)
C09D 11/107     (2014.01)
C09D 133/08     (2006.01)

(52) U.S. Cl.
CPC ........... C07C 69/604 (2013.01); C07C 271/24 (2013.01); C07D 493/04 (2013.01); C08G 18/4244 (2013.01); C08G 18/8175 (2013.01); C08G 63/47 (2013.01); C09D 11/107 (2013.01); C09D 133/08 (2013.01); C09D 167/07 (2013.01); C09D 175/16 (2013.01)

(58) Field of Classification Search
CPC .... C07C 69/604; C07C 271/24; C07C 493/04; C08G 18/4224; C08G 18/8175; C08G 63/47; C09D 11/107; C09D 133/08; C09D 167/07; C09D 175/16
See application file for complete search history.

(56) References Cited

U.S. PATENT DOCUMENTS

| 4,028,204 | A | 6/1977 | Rosen et al. |
| 5,580,941 | A | 12/1996 | Krause et al. |
| 5,783,616 | A | 7/1998 | Krause et al. |
| 5,847,065 | A | 12/1998 | Krause et al. |
| 5,854,191 | A | 12/1998 | Krause et al. |
| 5,854,321 | A | 12/1998 | Krause et al. |
| 5,917,031 | A | 6/1999 | Miura et al. |
| 5,919,834 | A | 7/1999 | Downs et al. |
| 6,069,187 | A | 5/2000 | Kusumoto et al. |
| 6,914,120 | B2 | 7/2005 | Germroth et al. |
| 7,250,209 | B2 | 7/2007 | Shibahara et al. |
| 7,723,461 | B1 | 5/2010 | Wagener et al. |
| 8,012,573 | B2 | 9/2011 | Kowata et al. |
| 2002/0013482 | A1 | 1/2002 | Brader et al. |
| 2002/0026028 | A1 | 2/2002 | Epple et al. |
| 2008/0020961 | A1 | 1/2008 | Rodrigues et al. |
| 2009/0018300 | A1 | 1/2009 | Bloom et al. |
| 2010/0136347 | A1 | 6/2010 | Simons et al. |
| 2011/0014139 | A1 | 1/2011 | Viala et al. |

(Continued)

FOREIGN PATENT DOCUMENTS

| BE | WO 2011058130 A1 * | 5/2011 | .......... C08G 63/672 |
| CN | 1177008 | 3/1998 | |
| CN | 1333303 | 1/2002 | |
| CN | 101353546 | 1/2009 | |
| CN | 101595158 | 12/2009 | |
| CN | 102686620 A * | 9/2012 | ........ C08F 222/1006 |
| DE | 10 2007 034 865 | 1/2009 | |

(Continued)

OTHER PUBLICATIONS

International Search Report issued Aug. 29, 2013 in International (PCT) Application No. PCT/EP2013/056125.

(Continued)

Primary Examiner — Sanza McClendon
(74) Attorney, Agent, or Firm — Wenderoth, Lind & Ponack, L.L.P.

(57) ABSTRACT

The present invention relates to a (meth)acrylated compound (A) prepared from: (i) a polyol constituent, (ii) a polyacid constituent and (iii) one or more (meth)acrylating compounds, wherein the polyol constituent comprises at least 30% by weight of one or more cyclic ether polyols, relative to the total weight of the polyol constituent, and wherein the compound (A) optionally further contains one or more moieties selected from the group consisting of (poly)caprolactone-containing moieties (ai), (poly)lactide- and/or (poly)glycolide-containing moieties (aii), moieties providing epoxide groups (aiii) and moieties providing alkylene oxide groups containing from 2 to 4 carbon atoms (aiv). The compounds of the invention are in particular suited for the making of radiation curable coating compositions and inks less prone to migration.

16 Claims, No Drawings

(56) References Cited

U.S. PATENT DOCUMENTS

| | | |
|---|---|---|
| 2011/0046225 A1 | 2/2011 | Dalle Carbonare |
| 2011/0092718 A1 | 4/2011 | Enger et al. |
| 2011/0163267 A1 | 7/2011 | Goldfinger et al. |
| 2012/0220676 A1 | 8/2012 | Moens |
| 2013/0144007 A1 | 6/2013 | Zastrow et al. |
| 2014/0004267 A1* | 1/2014 | Van Den Hugues ............... C09D 11/101 427/385.5 |
| 2014/0073716 A1 | 3/2014 | Cho et al. |
| 2014/0249285 A1 | 9/2014 | Palmese et al. |

FOREIGN PATENT DOCUMENTS

| | | | |
|---|---|---|---|
| EP | 0 648 234 | 9/1999 | |
| EP | 1 411 077 | 4/2004 | |
| EP | 1 762 600 | 3/2007 | |
| EP | 1 881 016 | 1/2008 | |
| EP | 2 226 171 | 9/2010 | |
| EP | 2 365 036 | 9/2011 | |
| TW | 201129866 A1 * | 9/2011 | ............ G03F 7/028 |
| WO | 01/25288 | 4/2001 | |
| WO | 01/27181 | 4/2001 | |
| WO | 02/38688 | 5/2002 | |
| WO | 03/078512 | 9/2003 | |
| WO | 2005/085369 | 9/2005 | |
| WO | 2006/102279 | 9/2006 | |
| WO | 2007/120459 | 10/2007 | |
| WO | 2008/000696 | 1/2008 | |
| WO | 2008/004002 | 1/2008 | |
| WO | 2008/015474 | 2/2008 | |
| WO | 2009/013064 | 1/2009 | |
| WO | 2009/115489 | 9/2009 | |
| WO | 2009/153168 | 12/2009 | |
| WO | 2011/004840 | 1/2011 | |
| WO | 2011/019557 | 2/2011 | |
| WO | 2011/048739 | 4/2011 | |
| WO | 2011/048750 | 4/2011 | |
| WO | 2011/058130 | 5/2011 | |
| WO | 2011/092328 | 8/2011 | |
| WO | 2011/128382 | 10/2011 | |
| WO | 2013/066461 | 5/2013 | |

OTHER PUBLICATIONS

International Search Report issued Jun. 20, 2013 in International (PCT) Application No. PCT/EP2013/056137.

* cited by examiner

RADIATION CURABLE (METH)ACRYLATED COMPOUNDS

The present invention relates to isosorbide-containing (meth)acrylated compounds, to their preparation and their uses.

BACKGROUND OF THE INVENTION

Radiation curable (meth)acrylated compounds may be produced commercially from petrochemical sources. The world's supply of petroleum is being depleted and eventually the demand for petrochemical derived products may outstrip the available supply. As a consequence, the market price of petroleum and petroleum derived products will increase making them less desirable.

Biology offers an attractive alternative for industrial manufacturers looking to reduce or replace their reliance on petroleum and petrochemical derived products. The replacement of petrochemicals and petrochemical derived products with products or feedstocks derived from biological resources (bioderived products) may offer many advantages. Products and feedstocks from biological sources are renewable. It may also be a response to the increasing demand for environmentally friendly products and to the price increase of petrochemical derived products.

Bioderived cyclic ether polyols obtained from various crops present a unique chemical structure that could fulfill the need for safer and more sustainable radiation curable resins. The non-aromatic cyclic structure of these derivatives provides high tensile modulus and high glass transition temperature. For instance, isosorbide di(meth)acrylates show unexpected high cure speeds combined with low viscosities and acceptable ink- or coating properties (WO 2011/048739 & WO 2011/048750). The applications requiring such performance are widespread in the industry.

There is however in particular a need for renewable compounds of oligomeric or polymeric nature that would be able to replace Bisphenol A. Today, an alternative for the reprotoxic Bisphenol A in e.g. packaging is a real market need.

SUMMARY OF THE INVENTION

Against this background we now provide, a (meth)acrylated compound (A) prepared from (i) a polyol constituent, (ii) a polyacid constituent and (iii) one or more (meth)acrylating compounds, wherein the polyol constituent comprises, relative to the total weight of the polyol constituent, at least 30% by weight of one or more cyclic ether polyols, and wherein the (meth)acrylated compound (A) optionally further contains one or more moieties selected from the group consisting of (poly)caprolactone-containing moieties (ai), (poly)lactide- and/or (poly)glycolide-containing moieties (aii), moieties providing epoxide groups (aiii) and moieties providing alkylene oxide groups containing from 2 to 4 carbon atoms (aiv).

Compounds (A) of the invention may present one or more of the following advantages:
- they are oligomeric or polymeric in nature and hence less prone to migration,
- they permit to achieve a fast and good curing,
- they are believed to be non-toxic,
- they may have a good solubility with other components of a UV formulation (e.g. with acrylates),
- they may have low viscosity,
- they may have glass transition temperatures within acceptable range,
- they may have low yellowing,
- they may present some resistance to oxygen inhibition,
- they permit to make radiation curable resins with a high renewable content.

In a further aspect of the present invention, the compositions (e.g. the inks, coating composition or adhesive) comprising compounds (A) of the present invention may present one or more of the following advantages:
- they can be used to make hard coats,
- they permit to achieve a more than acceptable hardness with materials having lower functionality,
- they can be used in food packaging due to their very low migration properties,
- they may have very good flow properties,
- they have high UV reactivity,
- they may have low viscosity,
- they may have low yellowing,
- they may have good mechanical properties once cured (e.g. good scratch resistance),
- they may provide excellent adhesion to for instance plastics,
- they can be cured in the presence of oxygen,
- they do not need to be formulated with Bisphenol A.

DETAILED DESCRIPTION OF THE INVENTION

In a first aspect of the invention, there is provided a (meth)acrylated compound (A) prepared from (i) a polyol constituent, (ii) a polyacid constituent and (iii) one or more (meth)acrylating compounds, wherein the polyol constituent comprises, relative to the total weight of the polyol constituent, at least 30% by weight of one or more cyclic ether polyols, and wherein the compound (A) optionally further contains one or more moieties selected from the group consisting of (poly)caprolactone-containing moieties (ai), (poly)lactide- and/or (poly)glycolide-containing moieties (aii), moieties providing epoxide groups (aiii) and moieties providing alkylene oxide groups containing from 2 to 4 carbon atoms (aiv).

Typically the (meth)acrylating compound (iii) comprises one (or essentially one) reactive group capable to react with hydroxyl groups or carboxylic acid groups as well as at least one (meth)acryloyl group. By "(meth)acryloyl" is meant acryloyl, methacryloyl or a mixture of both. Alternatively the (meth)acrylating compound may comprise at least one (meth)acryloyl group and one (or essentially one) reactive group capable of reacting with a linker that comprises one (or essentially one) reactive group capable of reacting with hydroxyl groups or with carboxylic acid groups.

By "(meth)acrylated" is meant to designate that compounds (A) of the invention contain one or more acryloyl groups, one or more methacryloly groups, or a mixture of both. Typically compounds (A) of the invention contain (meth)acryloyl groups at both ends of the molecule.

By a "(meth)acrylating compound" is meant to designate a compound that provides polymerizable (meth)acryloyl groups, preferably polymerizable acrylolyl groups. By "polymerizable" is meant to designate in particular that the (meth)acryloyl groups under the influence of irradiation and/or a (photo)initiator can undergo radical polymerization. By "moieties" is meant building blocks or monomeric units.

By a "(poly)caprolactone-containing moiety" is meant to designate a moiety containing one or more caprolactone units and/or one or more polycaprolactone units. Highly suitable are moieties (ai) that comprise at least one portion represented by Formula (1):

wherein u is an integer of from 2 to 5, preferably from 3 to 5; and t is an integer of from 1 to 10, preferably from 1 to 5, and most typically from 1 to 3. Moieties (ai) are typically selected from (poly)γ-butyrolactone moieties, (poly)δ-valerolactone moieties and/or (poly)ε-caprolactone moieties. Preferred are (poly)ε-caprolactone moieties and more in particular poly-ε-caprolactone moieties. Often t is then 1 or 2.

By a "(poly)lactide-containing moiety" is meant to designate a moiety containing one or more polylactide units and/or one or more lactide units. By a "(poly)glycolide-containing moiety" is meant to designate a moiety containing one or more polyglycolide units and/or one or more glycolide units. Typically moieties (aii) comprise at least one portion represented by Formula (2):

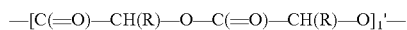

wherein t' is an integer from 1 to 10, and wherein each of R is selected from —H or —CH$_3$.

Typically t' is an integer from 1 to 5, more typically from 2 to 4. Typically R is —CH$_3$. The lactide can be a L-, meso- and/or D-lactide.

An example of a moiety providing epoxide groups (aiii) is a moiety derived from an epihalohydrin. Epihalohydrins are compounds having a halomethyl oxirane skeleton (scheme 1) wherein X is a halogen atom. Preferred epihalohydrins are epifluorohydrin, epichlorohydrin (also known as epichlorhydrin), epibromohydrin and/or epiiodohydrin. Most preferred is epichlorohydrin.

Scheme 1

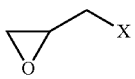

Examples of moieties (aiv) providing alkylene oxide groups containing from 2 to 4 carbon atoms are moieties derived from ethylene oxide, propylene oxide and/or butylene oxide. Preferred are moieties derived from ethylene oxide and/or propylene oxide.

In an embodiment of the invention one or more of the polyols used to prepare compounds (A) of the invention may be modified to contain one or more of the above moieties. Alternatively, or in addition, these moieties may be contained in the (meth)acrylating compounds (iii). Where present, however, these moieties preferably are contained in the polyester backbone only as this gave rise to better properties.

Compounds (A) according to the present invention can be prepared in various ways. One possibility is to have all reagents react in a one pot system. Alternatively, the compounds may be prepared by a process comprising a first step of preparing a polyester from a polyol constituent and a polyacid constituent as described, and a second step comprising the reaction of the polyester obtained in the first step with one or more suitable (meth)acrylating compounds. Typically compounds (A) of the invention are prepared by reacting compounds (i), (ii) and (iii) and possibly (iv), preferably under anhydrous conditions, and preferably at a temperature between 50° C. and 150° C., more preferably between 80° C. and 130° C., until the reaction is substantially complete. The reaction may be facilitated by the addition of from 5 to 40%, preferably from 15 to 25%, by weight, of a solvent in order to reduce the viscosity of the pre-polymer. The solvent is preferably heptane, hexane or toluene. During this process, it is common to use catalysts to accelerate esterification reactions. Typical catalysts are strong acids like alkyl- and/or aryl sulphonic acids that are typically used in concentrations ranging from about 0.1 to about 2 wt %, relative to the total weight of compounds (A). Typical inhibitors are phenolic antioxidants like hydroquinone, methylether hydroquinone and the like, which are typically used in concentrations ranging from about 0.01 to about 0.5 wt %, relative to the total weight of compounds (A).

Typically the polyol constituent (i) used to prepare compounds (A) of the invention comprises at least 32% by weight of one or more cylic ether polyols (i'), relative to the total weight of the polyol constituent. Preferably this amount is at least 33% by weight, more preferably at least 34% by weight, even more preferably at least 35% by weight, and most preferably at least 40% by weight. Often this amount is at least 50% by weight, typically at least 60% by weight, more typically at least 70% by weight. This amount may go up to 100% by weight, relative to the total weight of the polyol constituent.

By "polyols" is meant to designate organic compounds bearing two or more hydroxyl groups. Diols are often preferred.

Cyclic ether polyols (i') are compounds bearing at least one cyclic ether group and at least two hydroxyl groups. Preferred are bioderived cyclic ether polyols. Bioderived cyclic ether polyols are cyclic ether polyols derived from or synthesized by a renewable biological feedstock, such as, for example, agricultural, forestry, plant, bacterial or animal feedstock.

Examples of suitable cyclic ether polyols are e.g. anhydrohexitols. Anhydrohexitols are obtained by dehydration of hexitols like sorbitol (glucitol), mannitol, iditol, which are produced by reducing the carbonyl group of hexoses like glucose, mannose, idose that are typically derived from several biological feedstocks like wheat, corn, cellulose.

The double dehydration results in dianhydrohexitols. Usually the anhydrohexitol is a dianhydrohexitol like dianhydromannitol, dianhydrosorbitol, dianhydroiditol and mixtures thereof.

The dianhydrohexitol preferably is a dianhydrosorbitol, more in particular is isosorbide. A few companies have specialized in the production of dianhydrohextols like isosorbide, isomannide and isoidide.

Optionally one or more other polyols (ii') different from a cyclic ether polyol may be used to prepare compounds (A) of the invention. The amount of other polyols (ii') may vary from 0 to 68% by weight, relative to the total weight of the polyol constituent. Often this amount is at most 67%, usually at most 66%, more typically at most 65%, most typically at most 60%, by weight. More often this amount is at most 50%, more typically at most 40%, even more typically at most 30%, by weight. By polyols (ii') is meant to designate in particular polyols that are different from a dianhydrohexitol as specified above, and more in particular polyols that are different from a dianhydrosorbitol like isosorbide.

In a particular embodiment of the invention, the amount of cyclic ether polyols (i') is at least 75% by weight, often at least 80% by weight, more in particular at least 85% by weight, even more in particular at least 90% by weight, up to 99.9% by weight, more typically up to 99.5% by weight, relative to the total weight of the polyol constituent. Typically the cyclic ether polyol is a dianhydrohexitol, more in particular a dianhydrosorbitol, most in particular it is isosorbide. Examples of polyols (ii') that may be used in the context of the present invention include but are not limited to (poly)ethylene glycols (like for instance ethylene glycol, diethylene glycol and triethylene gycol); (poly)propylene glycols (like for instance proplylene glycol, dipropylene glycol and tripropylene glycol); 1,3-propanediol (neopentylglycol); 2-methyl-1,3-propanediol (MPD); 2-ethyl-2-butyl-1,3-propanediol; 1-ethyl-2-methyl-1,3-propanediol; 2-ethyl-2-methyl-1,3-propanediol; 1,3-butylene glycol; 1,4-butanediol; 2,3-butanediol; 2-butyl-2-ethyl-1,3 propanediol (BEPD); pentanediol; 2-methyl-2-ethyl-1,3-propane diol; 1,3-pentane diol; 2,2,4-trimethyl-1,3-pentane diol; hexyleneglycol; 1,6-hexanediol; 1,4-cyclohexanediol; 1,4-cyclohexanedimethanol; 3-hydroxy-2,2-dimethyl propyl 3-hydroxy-2,2-dimethyl-propanoate (hydroxylpivalyl hydroxypivalate (HPHP); the hydroxypivalate of neopentyl glycol); 2,2,4-trimethyl-1,3-pentanediol (TMPD); hydrogenated Bisphenol A; trimethylolpropane, pentaerythritol; ethoxylated and/or propoxylated forms of any of these (such as for instance propoxylated glycerol); and mixtures thereof (of any of the above). Often the polyols (ii') are diols. Examples of polyols (ii') of higher functionality that may be used in the context of the invention include but are not limited to: polyol R3540 from Perstorp. A more extensive list of other suitable polyols (ii') is provided in Table 1:

TABLE 1

| | Functionality | Hydroxy number (mg KOH/g) | Molecular weight (g/mol) | Viscosity (mPas, 23° C.) |
|---|---|---|---|---|
| Polyol R2395 | 2 | 395 | 276 | 350 |
| Polyol R 2490 | 2 | 490 | 220 | 170 |
| Polyol 3165 | 3 | 165 | 1014 | 350 |
| Polyol 3380 | 3 | 380 | 444 | 360 |
| Polyol 3610 | 3 | 610 | 275 | 700 |
| Polyol 3611 | 3 | 611 | 275 | 700 |
| Polyol 3940 | 3 | 940 | 179 | 4000 |
| Polyol 3990 | 3 | 990 | 170 | 4500 |
| Polyol R3215 | 3 | 215 | 795 | 340 |
| Polyol R3430 | 3 | 430 | 398 | 400 |
| Polyol R3530 | 3 | 530 | 308 | 2000 |
| Polyol R3540 | 3 | 540 | 311 | 550 |
| Polyol R3600 | 3 | 600 | 275 | 700 |
| Polyol 4290 | 4 | 290 | 797 | 450 |
| Polyol 4360 | 4 | 360 | 629 | 1300 |
| Polyol 4525 | 4 | 525 | 426 | 2600 |
| Polyol 4640 | 4 | 640 | 355 | 1100 |
| Polyol 4800 | 4 | 800 | 282 | 2200 |
| Polyol R4630 | 4 | 630 | 350 | 1500 |
| Polyol 4631 | 4 | 631 | 356 | 1500 |
| Polyol R6405 | 6 | 405 | 827 | 1900 |

Preferred polyols (ii') are propoxylated and/or ethoxylated glycerol, trimethylolpropane, polyol R3540 from Perstorp, pentaerythritol (such as PP50 from Perstorp), as well as mixtures of any of these.

The polyacid constituent (ii) used to prepare compounds (A) of the invention can comprise one or more "polyacids". By "polyacids" is meant to designate organic are used at all, dimethylesters and/or diethylesters are preferred. Preferred polyacids compounds bearing two or more carboxylic acid groups. The corresponding anhydrides or a suitable corresponding dialkylester of the polyacid may also be used. When dialkylesters are diacids (i.e., polycarboxylic acids bearing two carboxylic acid groups).

Any suitable polyacid may be used but often aliphatic polyacids and more in particular aliphatic diacids are used. Typically the aliphatic diacids used are linear chain aliphatic diacids. Typically one or more polyacids from the following list are used: succinic acid, adipic acid, glutaric acid, pimelic acid, suberic acid, azelaic acid, sebacic acid, 1,12-dodecanedioic acid, and dimer diacids such as Empol® 1018 or Pripol® 1013.

Examples of suitable anhydrides include but are not limited to succinic anhydride, maleic anhydride, phthalic anhydride, trimellitic anhydride and/or pyromellitic dianhydride. The following may also be used: itaconic acid, citraconic acid, mesaconic acid, phthalic acid, 1,4-cyclohexanedicarboxylic acid, 1,3-cyclohexanedicarboxylic acid, 1,2-cyclohexanedicarboxylic acid, citric acid, tartaric acid, trimellitic acid, pyromellitic acid, or the corresponding anhydrides (of any of these). Aromatic polyacids such as isophthalic acid, and/or terephthalic acid may also be used.

Preferred polyacids are phthalic anhydride, dimer diacids, succinic acid, succinic anhydride and/or adipic acid. Even more preferred are dimer diacids, succinic acid, succinic anhydride and/or adipic acid.

The choice of a suitable (meth)acrylating compound (iii) will be in function of the ratio of total polyols (i' and ii)/total polyacids (ii) used. Often this ratio is above 1.

Typically the (meth)acrylating compounds (iii) attach to the molecule's backbone via ester and/or carbamate groups. In certain embodiments of the invention a linker (for instance an anhydride) may be used to attach the (meth) acrylating compounds to the backbone of the molecule.

Below: some preferred modes of operating the invention for cases where the ratio of total polyols (i' and ii')/total polyacids (ii) is above 1. Often this ratio is from 2:1 to 6:5, most often this ratio is from 2:1 to 4:3. Typically (meth) acrylating compounds (iii) are then used that comprise reactive groups capable to react with hydroxyl groups. Most typically (meth)acrylating compounds (iii) are used that comprise essentially one (in particular one) reactive group capable to react with hydroxyl groups.

In a first variant of the invention, (meth)acrylating compounds (iii) are selected from an unsaturated acid and/or a suitable equivalent thereof. Examples of suitable equivalents are for instance the acyl halide of the unsaturated acid, the corresponding anhydride of the unsaturated acid and/or a lower alkyl ester of the unsaturated acid. With lower alkyl is meant a $C_1$-$C_4$ alkyl. Preferred for use in the invention are unsaturated monoacids (see e.g. Formula IV below). Particularly suited for use in the present invention are (meth) acrylic acid, a (meth)acrylic acid anhydride, a (meth)acrylic acid halide, and/or a lower alkyl ester of (meth)acrylic acid. Examples of suitable (meth)acrylic acid halides are (meth) acrylic acid chloride, (meth)acrylic acid bromide and/or (meth)acrylic acid iodide. By a lower alkyl ester is meant to designate in particular the lower alcohol ester of an unsaturated acid such as (meth)acrylic acid. The lower alcohol preferably is an aliphatic $C_1$-$C_4$ alcohol. Preferred lower alkyl esters are for instance methyl esters, ethyl esters, n-propyl esters and/or iso-propyl esters of (meth)acrylic acid. When a (meth)acrylic acid halide is used and/or a (meth)acrylic acid anhydride, it is desirable to work in a dehydrated state to avoid disassembly. Preferred for use in this first variant of the first embodiment is (meth)acrylic acid. More suitable examples are provided in the section around Formula IV below.

In a second variant of the invention, (meth)acrylating compounds (iii) are selected from the reaction products (or adducts) of at least one polyisocyanate (iv) and at least one compound (v) containing at least one reactive group capable to react with isocyanate groups and containing at least one (meth)acryloyl group.

By a polyisocyanate (iv) is meant to designate an organic compound containing at least two isocyanate groups. Typically the polyisocyanate contains not more than six isocyanate groups, more preferably not more than three isocyanate groups. Most typically it is a diisocyanate.

Polyisocyanates may be selected from one or more aliphatic, cycloaliphatic, aromatic and/or heterocyclic polyisocyanates well known in the art. Examples of aliphatic and cycloaliphatic polyisocyanates that may be used are: 1,6-diisocyanatohexane (HDI), 1,1'-methylene bis[4-isocyanatocyclohexane] (H12MDI), 5-isocyanato-1-isocyanatomethyl-1,3,3-trimethyl-cyclohexane (isophorone diisocyanate, IPDI). Aliphatic polyisocyanates containing more than two isocyanate groups are for example the derivatives of above mentioned diisocyanates like 1,6-diisocyanatohexane biuret and isocyanurate. Examples of aromatic polyisocyanates that may be used are 1,4-diisocyanatobenzene (BDI), 2,4-diisocyanatotoluene (TDI), 1,1'-methylenebis[4-isocyanatobenzene] (MDI), xylilene diisocyanate (XDI), 1,5-naphtalene diisocyanate (NDI), tolidine diisocyanate (TODD, tetramethylxylylene diisocyanate (TMXDI) and p-phenylene diisocyanate (PPDI). Other examples of polyisocyanates that may be used in the context of the invention are trimethylhexamethylenediisocyanate, 4,4'-diisocyanatodicyclohexylmethane, 4,4'-diisocyanatodiphenylmethane, the technical mixtures with 2,4-diisocyanatodiphenylmethane and also the higher homologues of above mentioned diisocyanates, 2,4-diisocyanatotoluene and technical mixtures of them with 2,6-diisocyanatotoluene, as well as the copolymerisation product of 3-isopropenyl-α,α'-dimethylbenzyl isocyanate (TMI).

Preferred are aliphatic polyisocyanates, most preferred are aliphatic diisocyanates.

Compounds (v) are compounds that contain at least one reactive group capable to react with isocyanate groups and at least one (meth)acryloyl group. Typically compounds (v) are end-capping agents that contain at least one acryloyl and/or methacryoyl group as well as one (or essentially one) nucleophilic function capable of reacting with isocyanate groups, such as a hydroxyl group. Other possible groups are amino and/or thiol groups. Hydroxyl groups though are preferred. Mono-(meth)acryloyl mono-hydroxy compounds as well as poly-(meth)acryloyl mono-hydroxy compounds can be used.

Useful compounds (v) include the esterification products of aliphatic and/or aromatic polyols with (meth)acrylic acid, said compounds (v) having a residual average hydroxyl functionality of about 1. The partial esterification products of (meth)acrylic acid with tri-, tetra-, penta- or hexahydric polyols or mixtures thereof are preferred. In this context, it is also possible to use reaction products of such polyols with ethylene oxide and/or propylene oxide. In this context, it is also possible to use the reaction products of such polyols with lactones, which add to these polyols in a ring-opening reaction. Examples of suitable lactones are γ-butyrolactone and, in particular δ-valerolactone and ε-caprolactone. Glycolides and lactides can be used for the same purpose. These modified or unmodified polyols are partly esterified with acrylic acid, methacrylic acid or mixtures thereof until the desired residual hydroxyl functionality is reached.

Compounds (v) obtained from the reaction of (meth)acrylic acid with aliphatic, cycloaliphatic or aromatic compounds bearing an epoxy functionality, forming a compound bearing a hydroxyl functionality together with at least one (meth)acrylic functionality can be used as well.

Other suitable compounds (v) are the (meth)acrylic esters with linear and branched polyols in which at least one hydroxy functionality remains free, like hydroxyalkyl(meth) acrylates having 1 to 20 carbon atoms in the alkyl group. Preferred molecules in this category are hydroxymethyl (meth)acrylate, hydroxyethyl(meth)acrylate, hydroxypropyl (meth)acrylate and/or hydroxybutyl(meth)acrylate. Preferred examples of poly-(meth)acryloyl hydroxylated compounds are compounds comprising at least two (meth) acryl functions such as glycerol diacrylate, trimethylolpropane diacrylate, glycerol diacrylate, pentaerythritol triacrylate, ditrimethylolpropane triacrylate, dipentaerythritol pentaacrylate and their (poly)ethoxylated and/or (poly) propoxylated equivalents. Of this category poly-(meth)acryloyl mono-hydroxy compounds are preferred. Though somewhat less preferred, compounds (v) may contain one or more of the moieties (ai) through (aiv) as described above. The latter are referred to as compounds (v').

Examples of suitable compounds (v') are hydroxyC$_{1-4}$alkyl(meth)acrylate-((poly)lactone)$_t$ compounds, wherein t is an integer of from 1 to 10, preferably from 1 to 5. Preferably the (poly)lactone is a (poly)caprolactone. Examples of useful compounds (v') in this category are Tone M100 (Dow Chemicals) and/or Bisomer PEMCURE 12A (Cognis). Other examples of suitable moieties (v') are hydroxyC$_{1-4}$alkyl(meth)acrylate-((poly)lactide)$_{t'}$ compounds, wherein t' is an integer between 1 and 10, preferably t' is between 1 and 5 and most preferably t' is between 2 and 4. Examples of useful compounds (v') in this category are the reaction products (or adducts) of a hydroxy(meth)acrylate (compound II) and for instance Galacid Slow release (GALACTIC SA), FUTERRO® Lactide LF (Futerro), PURALACT® L, PURALACT® D or PURASORB G (Purac), or mixtures of these (of any of these). The amount of hydroxy(meth)acrylates, in particular hydroxyalkyl (meth)acrylates (v) used for the synthesis of compounds (v') in this category is generally in the range from 5 to 80 wt % (relative to the total weight of these compounds v').

Preferred however are compounds (v) that do not contain any of the above moieties (ai) through (aiv).

In this second variant of the invention, the polyisocyanate (iv) most typically is a diisocyanate, and compound (v) a compound that contains essentially one (in particular one) reactive group capable to react with isocyanate groups as well as at least one (meth)acryloyl group.

In a third variant of the invention, compounds (A) of the invention are prepared from the reaction of a polyol constituent as described above, a polyacid as described above, at least one anhydride (vi), and at least one (meth)acrylating compound (vii) containing one epoxide group and one or more (meth)acryloyl groups. Compounds (A) according to this variant typically are prepared by a process comprising: a first step, comprising the reaction of a hydroxyl-terminated polyester prepared from a polyol constituent and a polyacid constituent as described above with an anhydride (vi), and a second step, comprising the reaction of the product obtained in the first step with a compound (vii) containing one epoxide group and one or more (meth)acryloyl groups.

Examples of anhydrides (vi) that may be used include but are not limited to succinic anhydride, maleic anhydride, phthalic anhydride, trimellitic anhydride and/or pyromellitic dianhydride. Preferred are succinic anhydride, maleic anhydride and/or phthalic anhydride. Most preferred is succinic anhydride. Examples of compounds (vii) that may be used are glycidyl(meth)acrylate and/or mono (meth)acrylated Bisphenol A diglycidylethers. Glycidyl(meth)acrylate is preferred.

Below some preferred modes of operating the invention for cases where the ratio of total polyols (i' and ii')/total polyacids (ii) is below 1. Typically (meth)acrylating compounds (iii) are then used that comprise reactive groups capable to react with carboxylic acid groups. Most typically (meth)acrylating compounds (iii) are used that comprise essentially one (in particular one) reactive group capable to react with carboxylic acid groups.

In a fourth variant of the invention, (meth)acrylating compounds (iii) are selected from compounds (vii) as described above.

In a fifth variant of the invention, the (meth)acrylating compounds (iii) are selected from compounds (v) as described above.

Blends (or mixtures) of compounds (A) according to any of the above variants can be used wherever wanted. Preferred however are compounds (A) according to the first and/or second variant as described above.

Preferred in the context of the present invention are compounds (A) that are represented by the general formula (I):

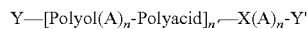

wherein:
Y and Y' independently are the residues of a (meth)acrylating compound;
X is the residue of a cyclic ether polyol, more in particular a dianhydrohexitol;
A represents the residue of a (poly)caprolactone, a (poly)lactide, a (poly)glycolide, a compound providing epoxide groups, and/or of an alkylene oxide group containing from 2 to 4 carbon atoms;
n and n' independently are integers from 0 to 10;
m is an integer from 1 to 5, preferably from 1 to 3.

Typically Y and Y' independently are chosen from (meth)acrylating compounds containing reactive groups capable to react with hydroxyl groups. Most typically Y and Y' contain e one (or essentially one) reactive group to react with hydroxyl groups. Preferred are compounds (iii) as described above for the first and/or second variant. Often Y and Y' are the same. Typically the dianhydrohexitol is isosorbide.

In this particular embodiment of the invention, the "Polyacid" may be any of the polyacids described above, with aliphatic diacids, more in particular linear chain aliphatic diacids or their equivalents being preferred. The "Polyol" can be selected from cyclic ether polyols (i') (in casu the dianhydrohexitols) and/or from polyols (ii') that are different from the cyclic ether polyols (in casu the dianhydrohexitols). Both have been described above.

In this particular embodiment of the invention, typically n and n' independently are integers from 0 to 5, more typically they are integers from 0 to 3. In a first variant of this embodiment, at least one of n and n' is 0, preferably both of n and n' are 0. In a second variant of this embodiment, at least one of n and n' is different from 0. In a third variant of this embodiment, n and n' independently are integers from 1 to 10, preferably from 1 to 5, typically from 1 to 3.

Particularly preferred are compounds (A) that are represented by the general formula (II):

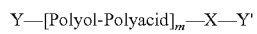

wherein X, Y, Y', the Polyol, Polyacid and m are as specified above. This formula corresponds to formula (I) above, wherein both n and n' are 0. Most preferably Y and Y' do not contain any of the moieties (ai) though (aiv) as identified above. Often Y and Y' are the same. Even more preferred are hence compounds (A) of the invention that are represented by the general formula (III):

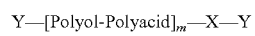

wherein X, Y, the Polyol, Polyacid and m are as specified above.

In a first variant of this embodiment, Y is the residue of an unsaturated monoacid—see the general formula (IV):

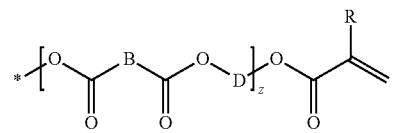

wherein z is an integer from 0 to 3, R is —H or —CH$_3$, B is the residue of an anhydride and D is the residue of a polyol, typically of a diol. Preferably z is 0 or 1.

In a particular embodiment of the invention, z is 0 and Y is the residue of (meth)acrylic acid, more in particular acrylic acid (see the first variant of the invention described above). In another embodiment of the invention, z>0, more in particular is 1, and Y is the residue of a mono-hydroxylated polyester (meth)acrylate. More in particular Y is then the residue of an adduct (or reaction product) of at least one anhydride (vi) with at least one compound (v) as described above. Particularly preferred compounds (v) are hydroxylated alkyl(meth)acrylates. In a second variant of this embodiment, Y is a residue represented by the general formula (V):

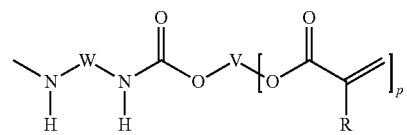

wherein W is the residue of a polyisocyanate (iv) as identified above, V is the residue of a polyol, R is —H or —CH$_3$, and p is an integer from 1 to 5, more preferably from 1 to 2. Most typically p is 1. Typically V is the residue of a diol.

Depending on the type of (meth)acrylating compounds (iii) used, compounds (A) of the invention can be polyester (meth)acrylates and/or urethane (meth)acrylates comprising at least one carbamate group. Urethane (meth)acrylates of the invention are particularly suited for use in coating applications. Polyester (meth)acrylates of the invention can be used in coating applications (including lacquers) or in inks.

Typically no compounds other than the ones described above are used for making compounds (A) to the invention.

Typically compounds (A) of the invention have a molecular weight (MW) of from 400 to 4.000 Daltons as measured by gel permeation chromatography using polystyrene standards. More typically the molecular weight is at least 500 Daltons, more preferably at least 1.000 Daltons. In general the molecular weight is at most 2.000 Daltons.

Preferably compounds (A) of the invention contain from 10 to 80% by weight of cyclic ether polyols (in casu dianhydrohexitols), relative to the total weight of the compound (A). Typically this amount is at least 20%, more preferably at least 25%, even more preferably at least 30%, by weight. Typically this amount is at most 70%, more preferably at most 50%, by weight, based on the total weight of compounds (A).

The present invention allows to make compounds (A) with high renewable content. For instance compounds (A) can be prepared wherein at least 25% by weight, even at least 30% by weight of the raw materials used to prepare the compounds is from renewable origin, relative to the total weight of compound (A). This amount can even be higher, for instance it can be at least 50% by weight, even at least 70% by weight.

Preferably compounds (A) of the invention have a viscosity as measured at 25° C. ranging from 400 to 40.000 mPa·s. Typically the viscosity is at most 25.000 mPa·s, more preferably at most 10.000 mPa·s.

Preferably compounds (A) of the invention are characterized by a glass transition temperature (Tg) of the cured material ranging from 35 to 100° C., as measured by Differential Scanning Calorimetry (e.g. according to ASTM E1640-09 with a heating gradient of 3° C. per minute). Typically the Tg is at least 50° C., more preferably at least 60° C. Typically the Tg is at most 160° C., more preferably at most 120° C.

An advantage of compounds (A) of the invention is their high cure speed. Compounds (A) of the invention are highly suitable for use in coating compositions. Coating compositions can be clear (e.g. lacquers) or pigmented. Compounds (A) of the invention are particularly suited for the preparation of hard coats. Compounds (A) of the invention are further also suitable for use in inks, varnishes and adhesives. Compounds (A) of the invention are also suitable for the making of polymer matrixes in composite materials (clear or pigmented). They are further suited for use in stereolithography applications.

A second aspect of the invention hence concerns a radiation curable composition comprising at least one compound (A) of the invention.

Typically compositions of the invention comprise, relative to the total weight of the composition, at least 5%, by weight, of compounds (A) of the invention. Typically this amount is at least 10%, usually at least 20%, more typically at least 50%, by weight. Typically this amount is at most 90%, more typically at most 70%, by weight.

Typically compositions of the invention further comprise at least one compound (B) that is different from compounds (A).

Typically compositions of the invention comprise, relative to the total weight of the composition, at least 10% by weight of compounds (B). Typically this amount is at least 20%, more typically at least 30%, by weight. Typically this amount is at most 50%, more typically at most 70%, by weight.

Preferred in the context of the invention are compositions that comprise, relative to the total weight of compounds (A) and (B), from 10 to 90%, by weight, of compounds (A), and from 90 to 10%, by weight, of compounds (B). More typically these compositions comprise, relative to the total weight of compounds (A) and (B), from 30 to 70%, by weight, of compounds (A), and from 70 to 30%, by weight, of compounds (B).

Compounds (B) may be selected from one or more of the following: (meth)acrylated compounds (B1) that have a molecular weight (MW) of from 200 to 5.000 Daltons; photoinitiators (B2), more in particular polymeric photoinitiators; and compounds (B3) that are represented by the general formula (VI):

wherein:
Y and Y' independently are the residues of a (meth)acrylating compound;
X is the residue of a cyclic ether polyol, more in particular a dianhydrohexitol;
A represents the residue of a (poly)caprolactone, a (poly)lactide, a (poly)glycolide, a compound providing epoxide groups, and/or of an alkylene oxide group containing from 2 to 4 carbon atoms; and
n' is an integer from 0 to 10.

More info on X, Y, Y', A and n' can be found above. Y and Y' typically are residues of (meth)acrylating compounds (iii) that comprise reactive groups capable of reacting with hydroxyl groups. In general, Y and Y' contain one (or essentially one) reactive group capable of reacting with hydroxyl groups. Most preferably Y and Y' are the same, and most preferably they are the residues of (meth)acrylic acid. Typically n' is an integer from 0 to 10. Often n' is at most 5 and preferably n' is at most 3. In a preferred variant n' is 0. The dianhydrohexitol typically is isosorbide. A preferred compound (B3) is the di(meth)acrylate of isosorbide. In another variant, n' is at least one and at most 10, preferably at most 5, most preferably at most 3. Compounds (B3) typically are different from compounds (B1).

Compounds (B1) typically have a molecular weight (MW), and more in particular a weight average molecular weight, of from 200 to 5.000 Daltons. Typically the MW of these compounds is at least 300 and more preferably at least 500 Daltons. Typically the MW of these compounds is at most 2.000 and more preferably at most 1.000 Daltons.

Compounds (B1) typically are oligomers or polymers, more typically they are oligomers.

Preferably compounds (B1) are selected from one or more of the following: polyester (meth)acrylates different from compounds (A), urethane (meth)acrylates different from compounds (A), alkoxylated (meth)acrylated oligomers, epoxy(meth)acrylates, aminated (meth)acrylates, (meth)acrylated (meth)acrylics, and (meth)acrylic (co)polymers (also referred to as full acrylics), inert polyesters that optionally are chlorinated.

Examples of suitable polyester (meth)acrylates are acrylated epoxidized soybean oil compounds like EBECRYL® 860 (Cytec), fatty acid containing polyester (meth)acrylates like EBECRYL® 870, EBECRYL® 657, EBECRYL® 450 (Cytec), and polyester (meth)acrylates like EBECRYL® 800, EBECRYL® 884, EBECRYL® 810 and EBECRYL® 830 (Cytec).

Examples of suitable epoxy(meth)acrylates are the di(meth)acrylate of diglycidyl ether of Bisphenol A (BADGED (M)A), and modifications thereof (see for instance EBECRYL® 3700 or EBECRYL® 600, EBECRYL® 3701, EBECRYL® 3703, EBECRYL® 3708 and EBECRYL® 3639 from Cytec). Examples of suitable urethane (meth)acrylates are EBECRYL® 284, EBECRYL® 264, EBECRYL® 210, EBECRYL® 230, EBECRYL® 1290 (Cytec). Examples of suitable aminated (meth)acrylates are EBECRYL® 80, EBECRYL® 81, EBECRYL® 83, EBECRYL® 7100, P115 and others. Examples of suitable (meth)acrylic (co)polymers that may be used are EBECRYL® 745 and/or EBECRYL® 1200. Examples of suitable inert polyesters include, but are not limited to EBECRYL® 525 and optionally chlorinated variants thereof (such as EBECRYL® 436 and others).

Examples of suitable polymeric photoinitiators (B2) that may be used in the context of the present invention are P36, P39 and the like.

Often compositions of the invention further comprise at least one compound (C) which is different from compounds (A) and (B). Compound (C) typically is a reactive diluting monomer. Compound (C) typically contains at least one active energy ray curable group, more in particular at least one (meth)acryloyl group, allyl group and/or vinyl group. Most typical are (meth)acryloyl groups.

Compounds (C) can be mono- and/or poly-functional (meth)acrylates. Especially the acrylated forms are used.

Examples of suitable compounds (C) include but are not limited to butyl(meth)acrylate, methyl(meth)acrylate, isobutyl(meth)acrylate, 2-ethylhexyl(meth)acrylate, cyclohexyl (meth)acrylate, n-hexyl(meth)acrylate, isobornyl(meth) acrylate, iso-octyl(meth)acrylate, n-lauryl(meth)acrylate, octyl/decyl(meth)acrylate, 2-hydroxyethyl(meth)acrylate, phenoxyethyl(meth)acrylate, nonylphenolethoxylate mono (meth)acrylate, 2-(-2-ethoxyethoxy)ethyl(meth)acrylate, 2-butoxyethyl(meth)acrylate, 1,6-hexanediol di(meth)acrylate (HDD(M)A), di or tri propylene glycol di(meth)acrylate (DPGD(M)A, TPGD(M)A), ethoxylated and/or propoxylated neopentylglycoldi(meth)acrylate, pentaerythritoltri (meth)acrylate (PETI(M)A) and the ethoxylated and/or propoxylated derivatives thereof, trimethylolpropanetri (meth)acrylate (TMPT(M)A) and the ethoxylated and/or propoxylated derivatives thereof, di-trimethylolpropanetri (meth)acrylate (diTMPT(M)A) glyceroltri(meth)acrylate and the ethoxylated and/or propoxylated derivatives thereof, bisphenol A di(meth)acrylate and the ethoxylated and/or propoxylated derivatives thereof, phenylglycidylether (meth)acrylate and the ethoxylated or/and propoxylated derivatives thereof, the (meth)acrylates obtained from the esterification with (meth)acrylic acid of aliphatic glycidyl ethers, especially those wherein the alkyl chain comprises from 6 to 24 carbon atoms, more preferably from 8 to 18 carbon atoms, and/or of glycidyl esters of saturated and unsaturated carboxylic acids, especially the glycidyl esters of long chain alkyl carboxylic acids wherein the alkyl chain comprises from 6 to 24 carbon atoms, more preferably from 8 to 18 carbon atoms. Preferred monomers (C) are di- and/or tri-(meth)acrylated monomers such as 1,6-hexanediol di(meth)acrylate (HDD(M)A), di or tri propylene glycol di(meth)acrylate (DPGD(M)A, TPGD(M)A), trimethylolpropanetri(meth)acrylate (TMPT(M)A) and the ethoxylated and/or propoxylated derivatives thereof, pentaerythritoltri (meth)acrylate (PETI(M)A) and the ethoxylated and/or propoxylated derivatives thereof, glyceroltri(meth)acrylate and the ethoxylated and/or propoxylated derivatives thereof, bisphenol A di(meth)acrylate and the ethoxylated and/or propoxylated derivatives thereof.

Typically compositions of the invention comprise, relative to the total weight of the organic non-volatile content of the composition, from 0 to 90% by weight, more in particular from 5 to 60% by weight of compounds (C). Where present, they are typically present in an amount of at least 5% by weight, generally at least 10% by weight, typically at least 20% by weight, more typically at least 30% by weight. Typically this amount is at most 60% by weight, more typically at most 40% by weight.

Compositions of the invention typically are cured by ultraviolet irradiation, generally in the presence of photoinitiator, which may be a polymeric photoinitiator (B2). They can also be cured by electron-beam irradiation, allowing the use of compositions free of photoinitiator. The compositions according to the invention are providing extremely rapid curing.

Photoinitiators where present typically are added in an amount of from 0.1 to 10 parts by mass per 100 parts by mass of photopolymerizable compounds. Examples of suitable photoinitiators include but are not limited to an aryl ketone type photoinitiator (such as an acetophenone, a benzophenone, an alkylaminobenzophenone, a benzyl, a benzoin, a benzoin ether, a benzoin dimethyl ketal, a benzoyl benzoate or an [alpha]-acyloxime ester), a sulfur-containing photopolymerization initiator (such as a sulfide or a thioxanthone), an acylphosphine oxide (such as an acyldiarylphosphine oxide) or other photopolymerization initiators. The photopolymerization initiator may be used as a mixture of at least two types thereof in combination. Further, the photopolymerization initiator may be used in combination with a photosensitizer such as an amine.

Alternatively, or in addition compositions of the invention may comprise at least one radical poloymerization initiator such as benzoyl peroxide, methyl cyclohexanone peroxide, cumene hydroperoxide, diisopropyl benzene peroxide, di-t-butyl peroxide, t-butyl peroxide and the like.

Compositions of the invention may further comprise, if the case requires, at least one of the following: an ultraviolet absorber, a photostabilizer, an antioxidant, a thermal polymerization inhibitor, a leveling agent, a defoaming agent, a thickener, a sedimentation-preventing agent, a pigment (organic coloring pigment, inorganic pigment), a coloring dye, an infrared absorber, a fluorescent brighter, a dispersant, an antistatic agent, an anti-fogging agent, and/or a coupling agent.

In a particular embodiment of the invention, the composition is a coating composition. Coating compositions of the invention can be applied to many different substrates including but not limited to paper, wood, metal, concrete, plastic etc.

Compositions of the invention in particular exhibit excellent adhesion on plastics, including polyvinylchloride, polycarbonate, polyethylene, acrylonitrile butadiene styrene copolymers etc. A preferred composition of the invention is a hard coat composition. By a hard coat composition in the context of the invention is meant to designate a composition that after cure has a Persoz hardness of at least 300 sec as measured at 25° C. on 40 micron films on glass.

In another particular embodiment of the invention the composition is an ink or an overprint varnish. The ink may be an ink used in lithographic, flexographic or inkjet applications. Inks of the invention may be used in the packaging industry, and are suitable for use on food packaging and more in particular food packaging for indirect food contact.

Curing time and conditions may vary according to the constituents of the composition, the thickness of the coating film and the active energy ray source used. Usually curing is achieved by irradiation for about 0.1 to about 60 seconds. Further, for the purpose of completing the curing reaction, a heat treatment may be carried out after irradiation with active energy rays. Compositions of the invention can be applied via any suitable technique used in the art including but are not limited to brushcoating, dipcoating, rollercoating, curtaincoating, spraycoating, vacuumcoating, flexo printing, gravure printing, lithographic printing, inkjet printing etc.

Compositions of the invention typically have a viscosity at 25° C. in the range of from 400 to 40.000 mPa·s. More preferably the viscosity at this temperature is in the range of from 400 to 20.000 mPa·s, most preferably from 400 to 10.000 mPa·s.

Though solvents may be used, compositions of the invention typically comprise at most 0.1% by weight of solvents. Usually this amount is at most 0.01% by weight, more preferably at most 0.001% by weight.

Compounds (A) of the invention typically are water-insoluble compounds. By "a water-insoluble compound" is meant to designate in the present invention that the compound is not self-emulsifiable or self-dispersible, but forms emulsions or dispersions in water or in aqueous solutions in the presence of a suitable external emulsifier. Typically such water-based compositions (emulsions or dispersions) would comprise at most 70% by weight of water. Usually this amount would be at most 65% by weight, more preferably at most 50% by weight. Yet a further aspect of the invention concerns a coating composition, ink, overprint varnish, or adhesive comprising at least one compound (A) according to the invention and/or at least one composition according to the invention. Provided are also coating compositions, inks, overprint varnishes or adhesives prepared from at least one compound (A) according to the invention and/or at least one composition according to the invention.

Yet another aspect of the invention concerns an article or a substrate on which a composition of the invention is applied, usually on at least one of its surfaces. In particular there is provided an article or substrate that is coated, either entirely or in part with a composition of the invention. The coating composition can be a hard coat composition as described above.

Yet another aspect of the invention concerns a food packaging printed with an ink or an overprint varnish of the invention. The food packaging in particular is one for indirect food contact.

Yet another aspect of the invention concerns a process for preparing a coated article or a substrate, comprising the steps of applying a coating composition of the invention on at least one of its surfaces, followed by radiation curing (e.g. via UV and/or electron beams). The coating composition can be a hard coat composition as described above.

Yet a further aspect of the invention concerns a composite composition (clear or pigmented) comprising at least one compound (A) according to the invention and/or at least one composition according to the invention, and at least one reinforcement material. The reinforcement material used can be fibrous or non-fibrous. Examples of non-fibrous materials include but are not limited to alumina trihydrate, barium sulfate, calcium carbonate, clay, glass microspheres, kaolin, metal fillers, carbon black, mica, organic fillers (wood flour, corncobs, rice/peanut hulls, and nutshells), silicas, talc, wollastonite and other nano-sized materials. Examples of fibrous materials include but are not limited to boron fibers, carbon fibers, aramid fibers, ceramic fibers, glass fibers, natural (such as but not limited to hemp, jute, flax, kenaf, leaf fibers) or synthetic fibers as described in U.S. Pat. No. 8,012,573, EP2226171, U.S. Pat. No. 7,250,209. Often a glass filler is used as reinforcement material. Examples of suitable glass fillers include but are not limited to glass fibers, glass cloths, nonwoven glass fabrics and other glass fiber cloths, glass beads, glass flakes, glass powders, milled glass species and so forth. Among them, glass fibers, glass cloths and nonwoven glass fabrics are preferred in view of their being highly effective in reducing the coefficient of linear expansion. Glass cloths are most preferred.

The invention will now be described in more details in the examples below, which in no way are intended to be limited.

Throughout the invention and in particular in the examples the following measuring methods have been applied.

Molecular weight determination via GPC: A small portion of sample is dissolved in tetrahydrofuran (THF) and injected into a liquid chromatograph (Merck-Hitachi L7100) equipped with 4 PLGeI Mixed-A polystyrene divinylbenzene GPC columns (300 mm×7.5 mm×20 µm). Typically polystyrene standards (typically in the Molecular Weight range: 200-7,500,000 Daltons) are added as internal standards. The components of the sample are separated by the GPC columns based on their molecular size in solution and detected by a Refractive Index detector. Data typically are gathered and processed by Polymer Laboratories Cirrus GPC software.

Cure speed: maximal belt speed under a given lamp, giving a full cured film, measured by solvent rubs (ADR: acetone double rubs). A minimum of 50 ADR is required for a fully cured coating with optimum performance.

Minimum cure dose: is the minimal UV energy required to cure a 10 µm coating that withstands a minimum of 50 acetone double rubs (ADR). The UV lamp chosen is a medium pressure mercury lamp of 80 W/cm output. The lower the dose to cure the coating, the better is the reactivity of the resin. The minimum cure dose corresponds to the cure speed for a given lamp and reflector.

Acetone double rubs: The fully cured character of the film is assessed by putting some talc on the surface and rubbing with a finger and then with a cotton. A mat aspect indicates a not fully cured film. The coating typically is also submitted to 50 double rubs with a wad of cotton drenched in acetone. A fully cured film is not visually affected by this test.

Persoz Hardness: pendulum hardness is measured for a 40 µm film on glass, cured 2× with the minimum cure dose, and is measured as the time (sec) required for the amplitude of the pendulum to drop from 12° to 4°. Harder coatings result in a longer oscillation time (less damping effect).

Mechanical properties: Stress strain curves from free films of about 100 µm are casted and cured with 5× the maximum cure speed of the formulation. Measurement conditions: Zwick Z010; temperature: 23° C.; relative humidity: 50%; Elongation speed: 50 mm/min; sample dimension: 30×10×0.08 mm; number of samples: 2-7.

Tg measurement: Tg is measured according ASTM E1640-09. The conditions are as follows:

DMA Q800 (TA instruments) tensile mode, frequency: 1 Hz, strain 10-30 tensile mode, frequency: 1 Hz, strain 10-30 µm, heatinprofile: −50 to 250° C. at 3°/min, sample dimension: 12×7.5×0.08 mm.

Viscosity: is measured at a fixed shear rate with a cone and plate type rheometer MCR100 (Paar-Physica). Transition temperatures (Tg) were measured by DSC following ASTM E1356-08.

Rheology (yield value, viscosity, shortness index): is measured using a cone and plate type rheometer MCR100 (Paar-Physica) following ISO 3219. The measurement geometry for measuring the (flexo) inks of the inventions was of a diameter of 25 mm and an angle of 1° for the cone. The measurement was a flow curve in controlled shear rate ranging from $D=0$ $s^{-1}$ (zero viscosity), $D=2.5$ $s^{-1}$ to $D=2500$ $s^{-1}$ at 25° C.

Optical density: The color density of the printed ink at constant film thickness is measured. In this case the ink is printed using a lab applicator and the color density is measured with a densitometer, which spectrophotometrically compares the reflected light to the incident light. Here, a Gretag Macbeth Spectroeye Spectrophotometer/Densitometer equipped with the appropriate filters was used to measure optical density. Film thickness (in g/m2) is determined by comparing the weight of the printed form or substrate before and after printing.

Gloss: Gloss is measured by means of a TR1-MICRO-GLOSS 20-60-85 SHEEN apparatus. Measurements are made with 60° geometry.

NCO content: The isocyanate content typically is followed by titration with an amine following ISO 11909

Chemical resistance: apply several spots of specific chemicals on the coating. Allow a good contact for a determined period of time. Clean the coating with a wad of cotton, drenched in a solvent if necessary. And Check the appearance of the coating. Score: 0 (bad) till 5 (excellent).

Renewable Raw Material Content: The Renewable Raw Material Content is calculated as the weight ratio of the renewable raw materials versus the total weight of raw materials.

EXAMPLES

Synthesis Example 1

Polyester Acrylate 1

400 gr Isosorbide (Posysorb P from Roquette), 582 gr Dimer Acid (Pripol 1017 from Croda), 295 gr Acrylic acid, 45 gr paratoluenesulphonic acid (65% in water), 1.5 gr methyl ether hydroquinone, 0.3 gr Copperoxide, 0.3 gr triphenylphosphite and 587 gr toluene are charged to a double-wall glass reactor equipped with a stirrer, a thermocouple attached to a thermoregulator, a gas inlet tube, a connection to vacuum and an distillation column. The mixture is then heated to a temperature of about 120° C. Esterification is continued until no more water is distilled over. The mixture then is cooled down to 60° C. and another 470 gr toluene are added. The mixture is washed three times with 200 gr water and dried by means of an azeotropic distillation. Subsequently the toluene is distilled of under reduced pressure of about 30 mm Hg and the reaction product is filtered. The polyester-acrylate thus obtained has a yellowish color and a viscosity of 10190 mPas at 25° C. The functionality of this polyester is 2.

Synthesis Example 2

Polyester Acrylate 2

548 gr Isosorbide (Posysorb P from Roquette), 182 gr Adipic Acid, 404 gr Acrylic acid, 35 gr methanesulphonic acid (70% in water), 1.4 gr methyl ether hydroquinone, 0.4 gr Copperoxide, 0.15 gr triphenylphosphite and 610 gr toluene are charged to a double-wall glass reactor equipped with a stirrer, a thermocouple attached to a thermoregulator, a gas inlet tube, a connection to vacuum and an distillation column. The mixture is then heated to a temperature of about 120° C. Esterification is continued until no more water is distilled over. The mixture then is cooled down to 60° C. and another 410 gr toluene are added. The mixture is washed three times with 200 gr water and dried by means of an azeotropic distillation. Subsequently the toluene is distilled of under reduced pressure of about 30 mm Hg and the reaction product is filtered. The polyester-acrylate thus obtained has a yellowish color and a viscsoity of 16.000 mPas at 25° C. The functionality of this polyester is 2.

Synthesis Example 3

Polyester Acrylate 3

288 gr Isosorbide (Posysorb P from Roquette), 465 gr propoxylated glycerol (MW: 260), 158 gr succinic Acid, 435 gr Acrylic acid, 41 gr methanesulphonic acid (70% in water), 1.5 gr methyl ether hydroquinone, 0.4 gr Copperoxide, 0.4 gr triphenylphosphite and 650 gr toluene are charged to a double-wall glass reactor equipped with a stirrer, a thermocouple attached to a thermoregulator, a gas inlet tube, a connection to vacuum and an distillation column. The mixture is then heated to a temperature of about 120° C. Esterification is continued until no more water is distilled over. The mixture then is cooled down to 60° C. and another 250 gr toluene are added. The mixture is washed three times with 200 gr water and dried by means of an azeotropic distillation. Subsequently the toluene is distilled of under reduced pressure of about 30 mm Hg and the reaction product is filtered. The polyester-acrylate thus obtained has a yellowish color and a viscsoity of 4100 mPas at 25° C. The functionality of this polyester is 3.

Synthesis Example 4

Polyester Acrylate 4

144 gr Isosorbide (Posysorb P from Roquette), 356 gr lactide, 0.5 gr stannous octoate, 0.5 gr tripenylphosphite and 0.25 gr hydroquinone monomethylether are charged to a double-wall glass reactor equipped with a stirrer, a thermocouple attached to a thermoregulator, a gas inlet tube, a connection to vacuum and an distillation column. The temperature is raised to 140° C. and kept at this temperature till the free lactide is less than 3%.

The mixture is cooled by adding 340 gr toluene, 58 gr succinic acid, 83 gr acrylic acid, 19 gr methanesulphonic acid (70% in water), 0.08 gr Copperoxide, 0.85 gr meHQ. The mixture is heated to 120° C. until no more water is distilled over. The mixture then is cooled down to 60° C. and another 180 gr toluene are added. The mixture is washed three times with 150 gr water and dried by means of an azeotropic distillation. Subsequently the toluene is distilled of under reduced pressure of about 30 mm Hg and the reaction product is filtered. The polyester-acrylate thus obtained has a yellowish color and a viscosity of 250.000 mPas at 60° C.

Synthesis Example 5

Polyester Acrylate 5

360 gr Isosorbide (Posysorb P from Roquette), 673 gr Dimer Acid (Pripol 1017 from Croda), 231 gr Acrylic acid, 39 gr paratoluenesulphonic acid (65% in water), 1.5 gr methyl ether hydroquinone, 0.3 gr Copperoxide and 590 gr toluene are charged to a double-wall glass reactor equipped with a stirrer, a thermocouple attached to a thermoregulator, a gas inlet tube, a connection to vacuum and an distillation column. The mixture is then heated to a temperature of about 120° C. Esterification is continued until no more water is distilled over. The mixture then is cooled down to 60° C. and another 460 gr toluene are added. The mixture is washed three times with 200 gr water and dried by means of an azeotropic distillation. Subsequently the toluene is distilled of under reduced pressure of about 30 mm Hg and the reaction product is filtered. The polyester-acrylate thus obtained has a yellowish color and a viscsoity of 23.300 mPas at 25° C. The functionality of this polyester is 2.

Synthesis Example 6

Urethane Acrylate 1

A polyester polyol a) is synthesized as follows:
A mixture of 113 gr Diethylene glycol (DEG), 195 gr isosorbide, 272 gr phthalic anhydride and 2.15 gr Fascat 4102 are heated to 220° C. in a double-wall glass reactor equipped with a stirrer, a distillation column connected to a water cooled condenser, an inlet for nitrogen and a thermocouple attached to a thermoregulator.

The reaction mixture is kept at 220° C. under atmospheric pressure till no water is distilling anymore. Reduced pressures is than applied gradually reaching a vacuum of −900 mmHg while the acid value is decreasing. Upon reaching an acid value of 10 mg KOH/g the mixture is cooled down to about 100° C.

The polyester obtained has an OH value of 90 mg KOH/g

An urethane acrylate b) is then made as follows:
209 gr Isophorone diisocyanate (IPDI) is charged into a double-wall glass reactor equipped with a stirrer. At 30° C., 110 gr hydroxyethyl acrylate, 0.3 gr DBTL and 0.3 gr methylether hydroquinone are fed into the reactor in 1 hr. An exothermic reaction with a temperature raise till 90° C. results in a NCO drop to 12.45% NCO.

Then, at 90° C., 548 gr of polyester a) and 183 gr hexanediol diacrylate (HDDA) are charged in the reactor. The reaction is continued till a NCO % of 0.15% is obtained.

An additional amount of 180 gr HDDA is added while the mixture is cooled.

The resin has a viscosity of 4400 mPas at 60° C.

TABLE 2

Summary of the synthesis examples

| Constituents | Ex1 Weight (g) | Ex2 | Ex3 | Ex4 | Ex5 | Ex6 |
| --- | --- | --- | --- | --- | --- | --- |
| isosorbide | 400 | 548 | 288 | 144 | 360 | 195 |
| Polyol R3540 | | | | | | |
| Glycerol PO | | | 465 | | | |
| DEG | | | | | | 113 |
| Dilactide | | | | 356 | | |
| Dimer diacid | 582 | | | | 673 | |
| Phthalic anhydride | | | | | | 272 |
| Adipic acid | | 182 | | | | |
| Succinic acid | | | 158 | 58 | | |
| IPDI | | | | | | 209 |
| HEA | | | | | | 110 |
| Acrylic acid | 295 | 404 | 435 | 83 | 231 | |
| % ISO on the polyol (wt %) | 100 | 100 | 44 | 100 | 100 | 81 |
| % ISO on compound (A) (wt %) | 31 | 48 | 25 | 23 | 28 | 30 |
| Viscosity (mPas, ° C.) | 10.190 (25° C.) | 16.000 (25° C.) | 4.100 (25° C.) | 250.000 (60° C.) | 23.300 (25° C.) | 4.400 (60° C.) |
| Dilution | 20 (1) | 25 (1) | 15 (1) | — | 8 (1) | 30 (2) |
| Renewable Raw Materials (wt %) | 85 | 57 | 28 | 77 | 89 | 30 |

(1): Isosorbide diacrylate
(2): Hexanediol diacrylate
ISO: isosorbide

Formulation Examples 1-3

Inks Prepared from Compounds of Example 1

Flexo inks were prepared from compounds obtained in Example 1. Composition and properties of the inks are summarized in Table 3 below. Properties of the inks were compared with standard flexo inks as documented below (FEx1R-FEx3R).

TABLE 3

| Formulation (in parts) | FEx1R | FEx1 | FEx2R | FEX2 | FEx3R | FEx3 |
| --- | --- | --- | --- | --- | --- | --- |
| EBECRYL ® 452 | 19 | | 19 | | | |
| Compound of Ex. 1 | | 19 | | 17 | | 12 |
| EBECRYL ® 3420 | | | | | 13 | |
| Isosorbide diacrylate | | 57 | | 59 | | 58.3 |
| EBECRYL ® 160 (TMPEO3TA) | 31 | | 31 | — | 45.3 | |
| EBECRYL ® 570 | 26 | | 26 | — | 12 | |
| ADDITOL ® S130 | 0.35 | 0.35 | 0.35 | 0.35 | 0.45 | 0.45 |
| Solsperse 39000 | 1.65 | 1.75 | 1.3 | 1.3 | 2.25 | 2.25 |
| Solsperse 5000 | | | 0.35 | 0.35 | | |
| Pigment red 57/1 | 14 | 14 | | | | |

TABLE 3-continued

| Formulation (in parts) | FEx1R | FEx1 | FEx2R | FEX2 | FEx3R | FEx3 |
|---|---|---|---|---|---|---|
| Pigment blue 15:3 | | | 14 | 14 | | |
| Pigment black 7 | | | | | 18 | 18 |
| PBZ | 3 | 3 | 3 | 3 | 3 | 3 |
| EDB | 5 | 5 | 5 | 5 | 5 | 5 |
| Irgacure 369 (BASF) | | | | | 1 | 1 |
| | 100 | 100 | 100 | 100 | 100 | 100 |
| Test results | | | | | | |
| Viscosity 2.5 1/s (mPa · s)-25° C. | 11000 | 4600 | 2390 | 5010 | 855 | 1700 |
| Viscosity 2500 1/s (mPa · s)-25° C. | 1000 | 1200 | 1030 | 1280 | 670 | 1200 |
| Shortness Index 2.5 - 2500 | 11 | 3.8 | 2.3 | 3.9 | 1.3 | 1.4 |
| Cure speed 120 W/cm- 1.5 g/m² - Air (m/min) | 10 | 120 | 20 | 100 | 40 | 90 |
| Total Energy dose (mJ/cm²) | 700 | 60 | 400 | 80 | 180 | 100 |
| Optical Density (1.5 g/m²) | 1.08 | 1.15 | 1.6 | 1.55 | 1.88 | 1.87 |
| Gloss (1.5 g/m²) | 70 | 90 | 95 | 96 | 78 | 70 |
| Renewable Raw Materials (wt %) | 4.5 | 43 | 4.5 | 40 | 0 | 41.5 |

EBECRYL ® 452: Fatty acid modified polyester acrylate, EBECRYL ® 3420: Modified epoxy acrylate, EBECRYL ® 570: Polyester in ethoxylated pentaerythritoltetracrylate, EBECRYL ® 160: Ethoxylated trimethylolpropane triacrylate, PBZ: Para-phenylbenzophenone, EDB: ethyl-4-dimethylaminobenzoate The above results show that compounds (A) of the invention have a good solubility with other components of a UV formulation and have very high reactivity. The cure speed is high and a lower total energy dose is required. Another advantage is that inks according to the invention allow a substantial amount of renewable raw materials to be used.

Formulation Example 4

Inks Prepared from Example 5

FEx4: Litho inks were prepared from compounds obtained in Example 5. Composition and properties of the inks are summarized in Table 4 below. Properties of the inks were compared with standard litho inks based on EBECRYL® 657 (FEx4R).

TABLE 4

| Formulation (in parts) | FEx4R | FEx4 |
|---|---|---|
| EBECRYL ® 657 | 38 | |
| Compound of Example 5 | | 50 |
| OTA | 12 | 0 |
| ADDITOL ® S120 | 1 | 1 |
| PLustalc H10-AW | 3 | 3 |
| PR57:1 | 18 | 18 |
| PI blend | 8 | 8 |
| Ebecryl 657 | 16 | |
| Compound ex. 5 | | 17.5 |
| OTA 480 | 4 | 2.5 |
| | 100 | 100 |
| Test results | | |
| Visco 2.5 1/s | 97.9 | 68.7 |
| Visco 100 1/s | 36.4 | 32.5 |
| SI 2.5 - 100 | 2.7 | 2.1 |
| Optical Density - 1.5 g/m² | 1.81 | 1.88 |
| Gloss - 1.5 g/m² 60° | 23 | 25 |
| Cure speed 120 W/cm (m/min) | 10 | 15 |
| Renewable Raw Materials (wt %) | 22 | 56 |

EBECRYL ® 657: Fatty acid polyester tetra acrylate, PLustalc: Micronized talcum from Mondo Minerals B.V OTA: Propoxylated glycerol tri-acrylate, PR57:1: pigment, PI: photoinitiator Also here excellent results and an improved cure speed combined with a remarkably high content of renewable raw materials.

Formulation Example 5

Coating Compositions Prepared from Compounds of Example 2

Coating compositions were prepared from compounds obtained in Example 2. Composition and properties of the inks are summarized in Table 5 below. Properties of the coating composition of the invention were compared with those of standard hard coatings based on EBECRYL® 800 (FEx5R).

10 micron thick coatings were applied with a barcoater on white paper for reactivity measurements and 20 micron thick coatings were applied on Lenetta paper for the chemical resistance measurements. Hardness is measured on glass (40 microns coating) as described above. The films are cured with a 80 Watt/cm Mercury medium pressure lamp and the properties are assessed on full cured films (min. required dose for 50 ADR).

TABLE 5

| Formulation (in parts) | Ex5R | Ex5 |
|---|---|---|
| EBECRYL ® 800 | 85 | |
| Compound of Example 2 | | 85 |
| TPGDA | 10 | 10 |
| BCPK | 5 | 5 |
| Test results | | |
| Viscosity at 25° C. (mPa · s) | 4540 | 3120 |
| Cure speed (m/min, 80 W/cm Hg lamp) | 15 | 30 |
| Persoz Hardness (sec) | 277 | 350 |
| Chemical resistance (1: low-5: excellent) | 5 | 5 |
| Functionality | 4 | 2 |
| Renewable Raw Materials (wt %) | 0 | 89 |

EBECRYL ® 800: Polyester acrylate, TPGDA: Tripropyleneglycol diacrylate, BCPK: Benzophenone 1-hydroxy-cyclohexylphenyl-ketone liquid mixture The above shows that with compositions of the invention a higher cure speed can be obtained. Similar properties were obtained with a lower functional material and with a substantial amount of renewable raw materials being used.

The invention claimed is:

1. A radiation curable composition comprising:
   a) at least one (meth)acrylated compound (A) prepared from: (i) a polyol constituent, (ii) a polyacid constituent and (iii) one or more (meth)acrylating compounds, wherein the polyol constituent comprises, relative to the total weight of the polyol constituent, at least 30% by weight of one or more dianhydrohexitols, and wherein the compound (A) optionally further contains one or more moieties selected from the group consisting of (poly)caprolactone-containing moieties (ai), (poly)lactide- and/or (poly)glycolide-containing moieties (aii), moieties providing epoxide groups (aiii) and moieties providing alkylene oxide groups containing from 2 to 4 carbon atoms (aiv), and
   b) at least one compound (B3) represented by the general formula (VI):

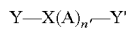
   Y—X(A)$_{n'}$—Y' wherein:
   Y and Y' independently are the residues of a (meth)acrylating compound;
   X is the residue of a dianhydrohexitol;
   A represents a residue of a (poly)caprolactone, a (poly)lactide, a (poly)glycolide, a compound providing epoxide groups, and/or of an alkylene oxide group containing from 2 to 4 carbon atoms; and
   n' is an integer from 0 to 10.

2. The radiation curable composition of claim 1, wherein the polyol constituent comprises from 40 to 100% by weight of dianhydrohexitols and, optionally, from 0 to 60% by weight of one or more polyols that are different from cyclic ether polyols.

3. The radiation curable composition of claim 1, wherein the dianhydrohexitol is isosorbide.

4. The radiation curable composition of claim 1, wherein the (meth)acrylating compounds (iii) are attached to the molecule's backbone via ester groups and/or via carbamate groups.

5. The radiation curable composition of claim 1, wherein the at least one (meth)acrylated comound (A) is represented by the general formula (I):

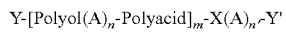
Y-[Polyol(A)$_n$-Polyacid]$_m$-X(A)$_{n'}$-Y' wherein:
Y and Y' independently are the residues of a (meth)acrylating compound;
X is the residue of a dianhydrohexitol;
A represents the residue of a (poly)caprolactone, a (poly)lactide, a (poly)glycolide, a compound providing epoxide groups, or of an alkylene oxide group containing from 2 to 4 carbon atoms;
n and n' independently are integers from 0 to 10; and
m is an integer from 1 to 5.

6. The radiation curable composition of claim 5, wherein the (meth)acrylating compounds are selected from: an unsaturated acid, an acyl halide of the unsaturated acid, and/or a $C_1$-$C_4$ alkyl ester of the unsaturated acid.

7. The radiation curable composition of claim 5, wherein the (meth)acrylating compound (iii) is (meth)acrylic acid.

8. The radiation curable composition of claim 5, wherein the (meth)acrylating compound (iii) is the reaction product of at least one polyisocyanate (iv) and at least one compound (v) containing at least one reactive group capable to react with isocyanate groups as well as at least one (meth)acryloyl group.

9. The radiation curable composition of claim 1 comprising at least 5% by weight of at least one compound (A).

10. The radiation curable composition of claim 1, further comprising at least one compound (B1) selected from polyester (meth)acrylates, epoxy (meth)acrylates, urethane (meth)acrylates and/or acrylic copolymers.

11. The radiation curable composition of claim 1 further comprising at least one photo-initiator.

12. The radiation curable composition of claim 1 which is a hard coat composition that after curing has a Persoz hardness of at least 300 sec as measured at 25° C. on 40μ films on glass.

13. The radiation curable composition of claim 1 which is an ink.

14. An article or substrate, having applied to a least one of its surfaces the radiation curable composition of claim 1.

15. The radiation curable composition of claim 1, wherein n' is 0.

16. The radiation curable composition of claim 11, wherein the photo-initiator is a polymeric photo-initiator (B2).

* * * * *